US012746317B2

(12) United States Patent
Abedin

(10) Patent No.: US 12,746,317 B2
(45) Date of Patent: Sep. 29, 2026

(54) SYSTEMS AND METHODS FOR RETURNING TREATED MONONUCLEAR CELLS TO A BLOOD SOURCE

(71) Applicant: Fenwal, Inc., Lake Zurich, IL (US)

(72) Inventor: Tanima Jahan Abedin, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 1690 days.

(21) Appl. No.: 16/149,538

(22) Filed: Oct. 2, 2018

(65) Prior Publication Data

US 2019/0099544 A1 Apr. 4, 2019

Related U.S. Application Data

(60) Provisional application No. 62/567,026, filed on Oct. 2, 2017.

(51) Int. Cl.

| | |
|---|---|
| ***A61M 1/36*** | (2006.01) |
| ***A61K 35/15*** | (2025.01) |
| ***A61K 35/17*** | (2025.01) |
| ***A61M 1/02*** | (2006.01) |
| ***A61M 1/38*** | (2006.01) |

(52) U.S. Cl.

CPC ........ *A61M 1/3683* (2014.02); *A61M 1/0209* (2013.01); *A61M 1/362227* (2022.05); *A61M 1/36225* (2022.05); *A61M 1/3643* (2013.01); *A61M 1/3644* (2014.02); *A61M 1/3693* (2013.01); *A61M 1/38* (2013.01); *A61K 35/15* (2013.01); *A61K 35/17* (2013.01); *A61M 2202/0407* (2013.01); *A61M 2202/0415* (2013.01); *A61M 2202/0427* (2013.01); *A61M 2202/0429* (2013.01); *A61M 2202/0439* (2013.01); *A61M 2202/0443* (2013.01); *A61M 2202/0447* (2013.01); *A61M 2205/051* (2013.01); *A61M 2205/50* (2013.01)

(58) Field of Classification Search

CPC ...................................................... A61K 35/15

See application file for complete search history.

(56) References Cited

U.S. PATENT DOCUMENTS

| | | | | |
|---|---|---|---|---|
| 4,568,328 | A * | 2/1986 | King | A61M 1/3683 D24/169 |
| 4,623,328 | A | 11/1986 | Hartranft | |
| 5,360,542 | A | 11/1994 | Williamson, IV et al. | |
| 5,868,696 | A | 2/1999 | Giesler et al. | |
| 6,027,657 | A | 2/2000 | Min et al. | |
| 7,433,030 | B2 | 10/2008 | Waldo et al. | |
| 2006/0155236 | A1 * | 7/2006 | Gara | A61M 1/362261 604/4.01 |
| 2008/0241815 | A1 | 10/2008 | Edelson et al. | |
| 2018/0256805 | A1 * | 9/2018 | Nguyen | A61M 1/362265 |

FOREIGN PATENT DOCUMENTS

| | | | |
|---|---|---|---|
| EP | 2641623 | A1 | 9/2013 |
| WO | 1999003976 | A2 | 1/1999 |
| WO | 2016205511 | A1 | 12/2016 |

OTHER PUBLICATIONS

Durazzo et al. "Induction of monocyte-to-dendritic cell maturation by extracorporeal photochemotherapy: initiation via direct platelet signaling." Transfusion and Apheresis Science 50.3 (2014): 370-378. (Year: 2014).*

Girardi et al. "Transimmunization for cutaneous T cell lymphoma: a Phase I study." Leukemia & lymphoma 47.8 (2006): 1495-1503. (Year: 2006).*

Florek, M., et al. "Autologous apoptotic cells preceding transplantation enhance survival in lethal murine graft versus-host models . . ." Blood. Sep. 11, 2014. vol. 124, No. 11.

Partial European Search Report for counterpart EP Application No. 18196602.9 (Feb. 15, 2019) (18 pages).

* cited by examiner

*Primary Examiner* — Emily A Cordas

(74) *Attorney, Agent, or Firm* — Cook Alex Ltd.

(57) ABSTRACT

A method for treating mononuclear cells for an extracorporeal photopheresis procedure, driven and adjusted by a microprocessor-based controller, comprising the steps of priming a fluid circuit with priming fluid, directing whole blood derived from a blood source into the fluid circuit, separating the whole blood into a red blood cell component, a mononuclear cell component, and a plasma component, returning a first portion of the red blood cell component and a first portion of the plasma component to the whole blood, adding a photoactivation agent to the mononuclear cell component to create an agent-added mononuclear cell component, irradiating the agent-added mononuclear cell component to create a photoactivated mononuclear cell component, and incubating for a period of time a first portion of the photoactivated mononuclear cell component to create an incubated photoactivated mononuclear cell component.

20 Claims, 7 Drawing Sheets

SYSTEMS AND METHODS FOR RETURNING TREATED MONONUCLEAR CELLS TO A BLOOD SOURCE

CROSS-REFERENCE TO RELATED APPLICATIONS

This application claims the benefit of U.S. Provisional Patent App. No. 62/567,026 filed Oct. 2, 2017, which is expressly incorporated herein by reference in its entirety.

FIELD OF THE DISCLOSURE

The present disclosure relates generally to systems and methods of performing extracorporeal photopheresis of mononuclear cells and, in particular to systems and methods for reinfusing treated mononuclear cells to a blood source.

BACKGROUND

Whole blood is made up of various cellular and non-cellular components such as red cells, white cells and platelets suspended in its liquid component, plasma. Whole blood may be separated into its constituent components (cellular, liquid or other), and the separated component(s) may be administered to a patient in need of that particular component or components.

The administration of blood and/or blood components is common in the treatment of patients suffering from disease. Rather than infuse whole blood, individual components may be administered to the patient(s) as their needs require. For example, administration (infusion) of platelets may often be prescribed for cancer patients whose ability to make platelets has been compromised by chemotherapy. Infusion of white blood cells (i.e., mononuclear cells) after the cells have undergone some additional processing or treatment may also be prescribed for therapeutic reasons, including treatment of diseases that specifically involve the white blood cells. Thus, it may be desirable to separate and collect the desired blood component from whole blood and then treat the patient with the specific blood component. The remaining components may be returned to the patient or retained for other uses.

There are several diseases or disorders which are believed to primarily involve mononuclear cells, such as cutaneous T-cell lymphoma, organ allograft rejection after transplantation and autoimmune diseases such as rheumatoid arthritis and systemic sclerosis, among others.

Cutaneous T-cell lymphoma (CTCL) is a term that is used to describe a wide variety of disorders. Generally, CTCL is a type of cancer of the immune system where T-cells (a type of mononuclear cell) mutate or grow in an uncontrolled way, migrate to the skin and form itchy, scaly plaques or patches. More advanced stages of the disease also affect the lymph nodes. Therapeutic treatment options for CTCL have previously been limited. While chemotherapy has been utilized, this particular form of treatment also has many associated undesirable side effects, such as lowered resistance to infection, bleeding, bruising, nausea, infertility and hair loss, just to name a few.

Organ allograft rejection may be characterized as the rejection of tissues that are foreign to a host, including transplanted cardiac tissue as well as lung, liver and renal transplants. Immunosuppression drug therapy following transplantation is common. However, there are potential drawbacks including reoccurring infection due to the compromised competence of the immune system caused by this type of therapy.

Similarly, graft versus host disease (GVHD) is a complication that can occur after a stem cell or bone marrow transplant in which the newly transplanted material attacks the transplant recipient's body. The differences between the donor's cells and recipient's tissues often cause T-cells from the donor to recognize the recipient's body tissues as foreign, thereby causing the newly transplanted cells to attack the recipient. GVHD may complicate stem cell or bone marrow transplantation, thereby potentially limiting these life-saving therapies. Therefore, after a transplant, the recipient may be administered a drug that suppresses the immune system, which helps reduce the chances or severity of GVHD.

Autoimmune diseases, including rheumatoid arthritis (RA) and progressive systemic sclerosis (PSS), can be characterized by an overactive immune system which mistakes the body's own tissues as being a foreign substance. As a result, the body makes autoantibodies that attack normal cells and tissues. At the same time, regulatory T-cells, which normally function to regulate the immune system and suppress excessive reactions or autoimmunity, fail in this capacity. This may lead to among other things, joint destruction in RA and inflammation of the connective tissue in PSS.

SUMMARY

According to an exemplary embodiment, the present disclosure is directed to a method for treating mononuclear cells for an extracorporeal photopheresis procedure, driven and adjusted by a microprocessor-based controller, comprising the steps of priming a fluid circuit with priming fluid, directing whole blood derived from a blood source into the fluid circuit, separating the whole blood into a red blood cell component, a mononuclear cell component, and a plasma component, returning a first portion of the red blood cell component and a first portion of the plasma component to the whole blood, adding a photoactivation agent to the mononuclear cell component to create an agent-added mononuclear cell component, irradiating the agent-added mononuclear cell component to create a photoactivated mononuclear cell component, and incubating for a period of time a first portion of the photoactivated mononuclear cell component to create an incubated photoactivated mononuclear cell component.

According to an exemplary embodiment, the present disclosure is directed to a system for treating mononuclear cells for an extracorporeal photopheresis procedure, comprising a disposable fluid circuit comprising a product container configured to receive a mononuclear cell component, a priming fluid container configured to receive albumin and/or a blood component for priming the disposable fluid circuit. The system also comprises a separator configured to work in association with the disposable fluid circuit, the separator comprising a chamber configured to rotate about a rotational axis and convey whole blood into an inlet region of the chamber for separation into a red blood cell component, a plasma component, and the mononuclear cell component. The system also comprises a microprocessor-based controller in communication with the separator. The controller is configured to direct the priming fluid from the priming fluid container through the disposable fluid circuit, direct whole blood derived from a blood source into the disposable fluid circuit while returning a portion of the priming fluid to the blood source, separate the whole blood into the red blood cell component, the mononuclear cell component, and the plasma component, return a first portion of the red blood cell component and a first portion of the plasma component to the blood source to the whole blood, retain a second portion of the red blood cell component and a second portion of the plasma component within the fluid circuit without returning to the blood source, direct the mononuclear cell component to the product container, irradiate the product container comprising the mononuclear cell component and a photoactivation agent to create a photoactivated mononuclear cell component, and reinfuse the photoactivated mononuclear cell component to the blood source.

According to an exemplary embodiment, the present disclosure is directed to a method for treating mononuclear cells for an extracorporeal photopheresis procedure, driven and adjusted by a microprocessor-based controller. The method comprises the steps of directing whole blood derived from a blood source into a fluid circuit, separating the whole blood into a red blood cell component, a mononuclear cell component, and a plasma component, returning a first portion of the red blood cell component and a first portion of the plasma component to the whole blood, retaining a second portion of the red blood cell component and a second portion of the plasma component within the fluid circuit, adding a photoactivation agent to the mononuclear cell component to create an agent-added mononuclear cell component, irradiating the agent-added mononuclear cell component to create a photoactivated mononuclear cell component comprising apoptotic T-cells and monocytes, reinfusing into the blood source the second portion of the red blood cell component and the second portion of the plasma component, incubating for a period of time a portion of the photoactivated mononuclear cell component to induce differentiation of the monocytes into dendritic cells, disconnecting the blood source from the fluid circuit while the portion of the photoactivated mononuclear cell component is incubating, and reinfusing a portion of the incubated photoactivated mononuclear cell component to the blood source.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

Figure 1:
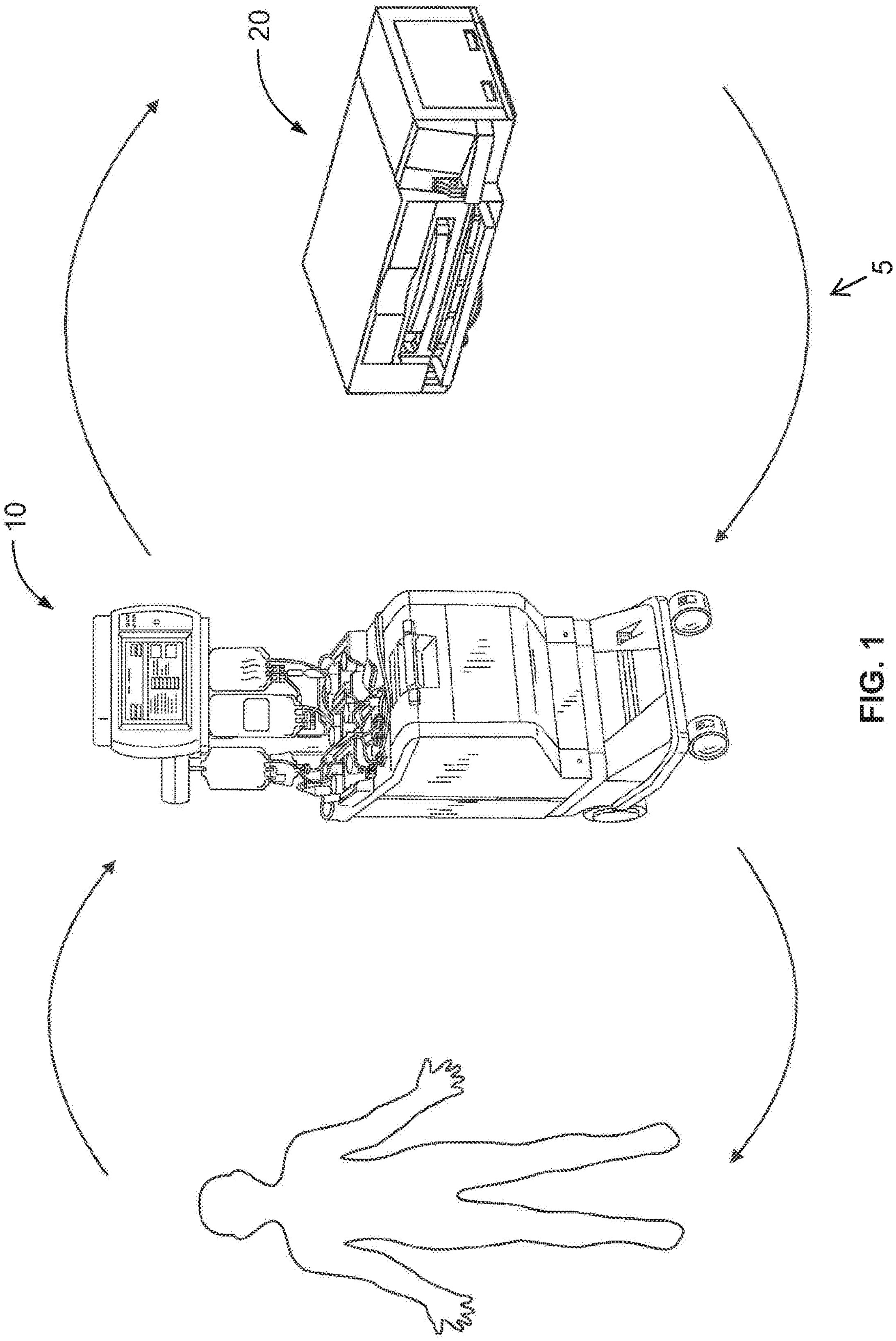
FIG. 1 is a diagram generally showing mechanical components of a photopheresis treatment device, according to an exemplary embodiment.

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Where existing therapies for treating one or more diseases may result in certain unintended side effects, additional treatment may be desired or required. One procedure which has been shown to be effective in the treatment of diseases and/or the side effects of existing therapies involving mononuclear cells is extracorporeal photopheresis or "ECP". Extracorporeal photopheresis (also sometimes referred to as extracorporeal photochemotherapy) is a process that includes: (1) collection of mononuclear cells (MNC) from a blood source (e.g., patient, donor, blood container, etc.), (2) photoactivation treatment of the collected MNC cells; and (3) re-infusion of the treated cells (MNC) back to the blood source. More specifically, ECP involves the extracorporeal exposure of peripheral blood mononuclear cells combined with a photoactive compound, such as 8-methoxypsoralen or "8-MOP" which is then photoactivated by ultraviolet light, followed by the re-infusion of the treated mononuclear cells. The combination of 8-MOP and UV radiation may cause apoptosis or programmed cell death of ECP-treated T-cells.

During ECP treatment, photoactivation is known to cause 8-MOP to irreversibly covalently bind to the DNA strands contained in the T-cell nucleus. When the photochemically damaged T-cells are reinfused, cytotoxic effects are induced. For example, a cytotoxic T-cell or "CD8+ cell" releases cytotoxins when exposed to infected or damaged cells or otherwise attacks cells carrying certain foreign or abnormal molecules on their surfaces. The cytotoxins target the damaged cell's membrane and enter the target cell, which eventually leads to apoptosis or programmed cell death of the targeted cell. In other words, after the treated mononuclear cells are returned to the body, the immune system recognizes the dying abnormal cells and begins to produce healthy lymphocytes (T-cells) to fight against those cells.

Extracorporeal photopheresis may also induce monocytes (a type of mononuclear cell) to differentiate into dendritic cells capable of phagocytosing and processing apoptotic T-cells. When these activated dendritic cells are re-infused into systemic circulation, they may cause a systemic cytotoxic CD8+ T-lymphocyte-mediated immune response to the processed apoptotic T-cell antigens like that described above. In some embodiments, it may be desirable to incubate the apoptotic T-cells with the monocytes prior to reinfusion in order to optimize differentiation into dendritic cells.

ECP may result in an immune tolerant response in the patient. For example, in the case of graft versus-host disease, the infusion of apoptotic cells may stimulate regulatory T-cell generation, inhibit inflammatory cytokine production, cause the deletion of effective T-cells and result in other responses. See Peritt, "Potential Mechanisms of Photopheresis in Hematopoietic Stem Cell Transplantation," Biology of Blood and Marrow Transplantation 12:7-12 (2006).

Figure 2:
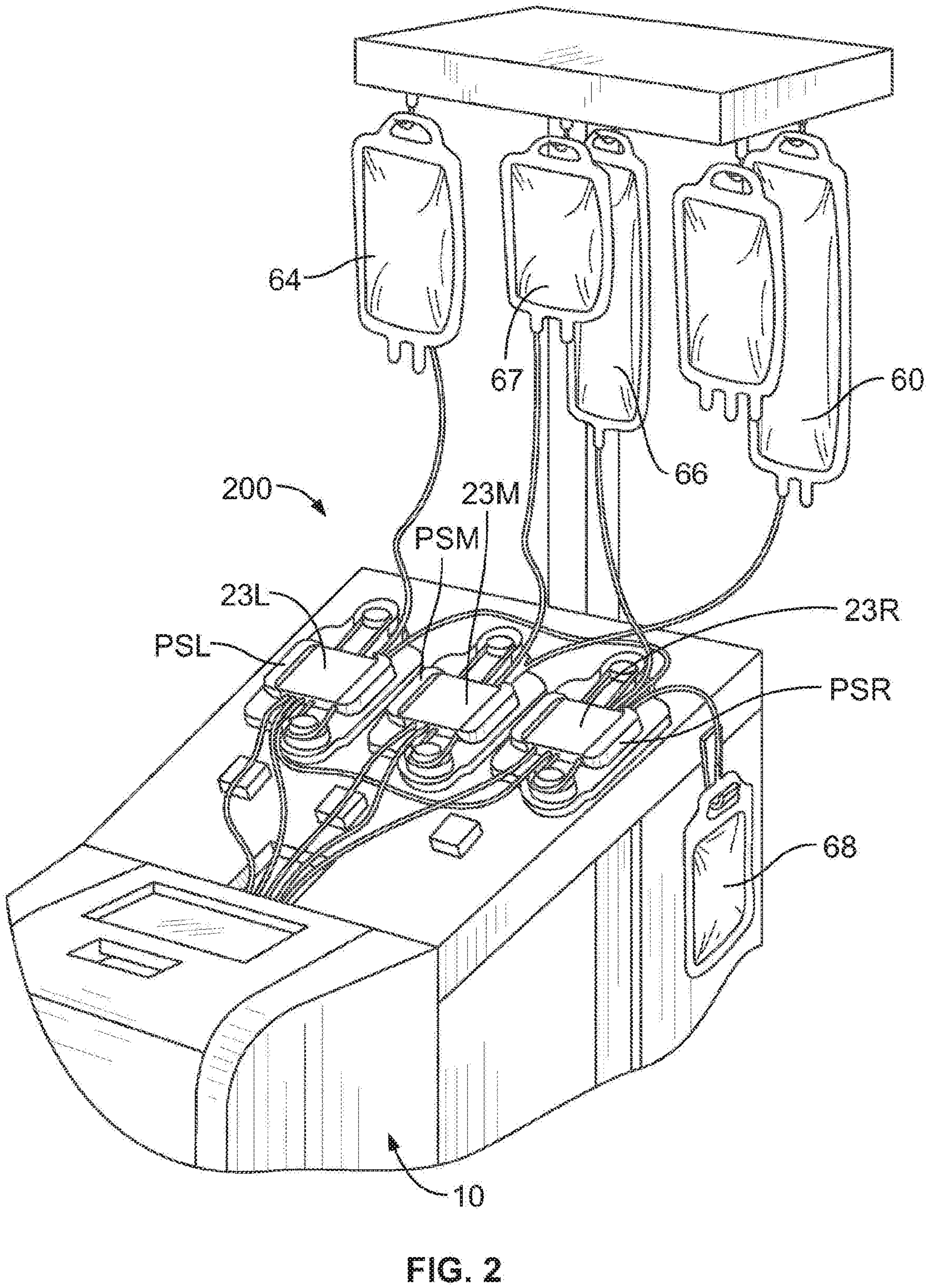
FIG. 2 is a partial perspective view of an apheresis separator useful in the methods and systems described herein, according to an exemplary embodiment.
Figure 4:
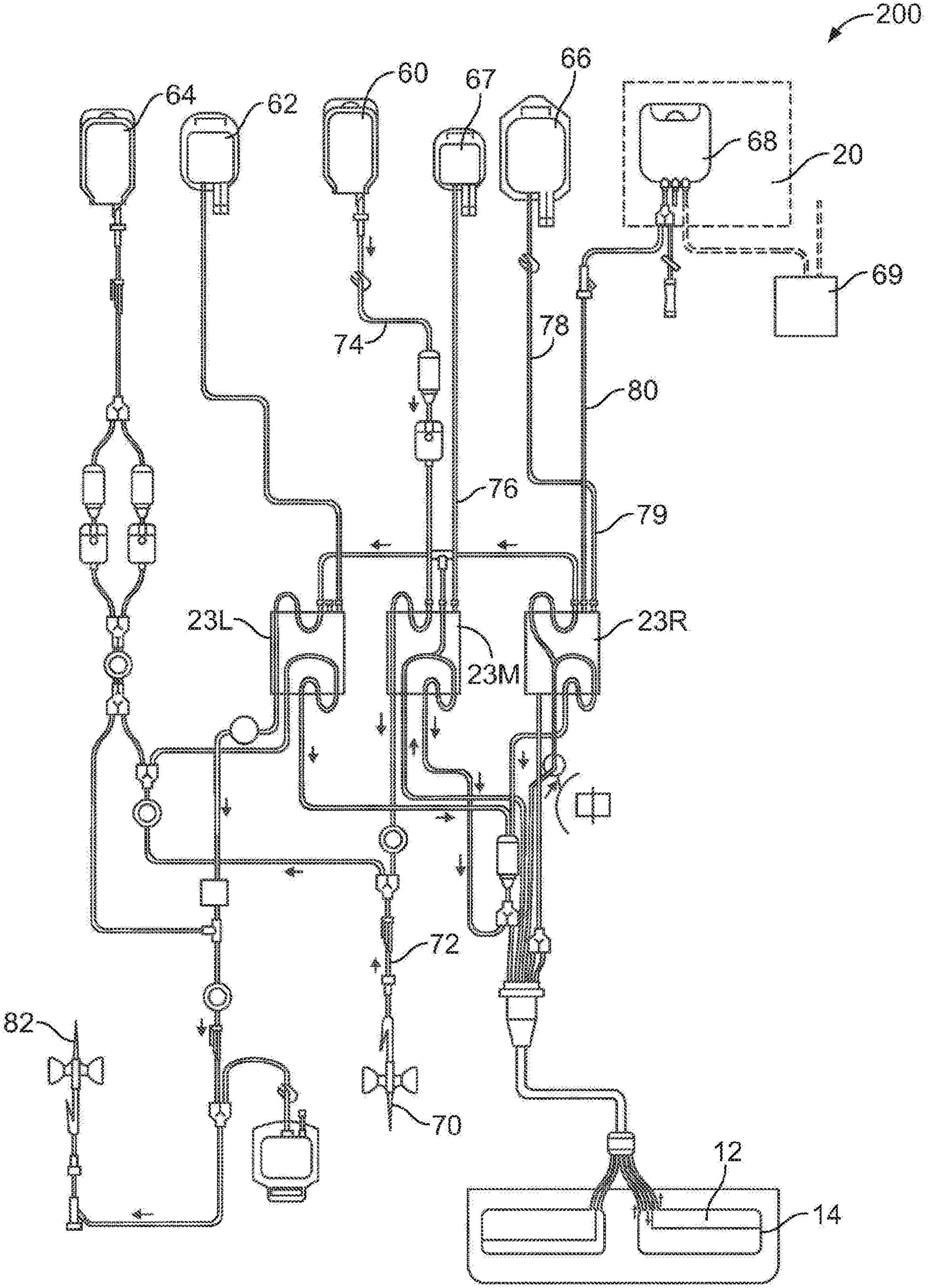
FIG. 4 is a diagram of a fluid circuit useful in the collection, treatment and reinfusion of target cells, according to an exemplary embodiment.

FIG. 1 shows, in general, the mechanical components that make up an ECP system 5 and that may be used in one or more of the systems and methods described herein. The system 5 may include a separation component 10 and a treatment (i.e., irradiation) component 20. Irradiation component 20 may be independent and housed separately from the separation component 10, or components 20 and 10 may be integrated into a single device. In an embodiment in which components 20 and 10 are housed separately, the separation device 10 and irradiation device 20 may be located adjacent to each other, allowing an operator or clinician to have access to both devices during a particular treatment procedure. A blood source may be connected to a fluid circuit 200 as shown in FIGS. 1, 2, 4 that provides a sterile closed pathway between separation component 10 and irradiation component 20 and may be cooperatively mounted on the hardware of the separation device 10. The separation device 10 may have one or more features of an apheresis device, such as a system marketed as the AMICUS® separator by Fenwal, Inc. of Lake Zurich, Illinois, as described in greater detail in U.S. Pat. No. 5,868,696, which is hereby incorporated herein by reference in its entirety, although any suitable separation device may be used.

With reference to FIG. 1, whole blood may be withdrawn from the blood source and introduced into the separation component 10 where the whole blood is separated to provide a target cell population. In one embodiment, the target cell population may be mononuclear cells (MNCs) or MNCs of a particular type (lymphocytes, monocytes, and/or dendritic cells, etc.). Other components separated from the whole blood, such as red blood cells (RBCs), plasma, and/or platelets may be returned to the blood source or collected in pre-attached containers of the blood processing set.

The separated target cell population, e.g., mononuclear cells, may then be treated and irradiated in treatment component 20. As discussed above, treatment of mononuclear cells may involve the photoactivation of a photoactive agent that has been combined with the mononuclear cells. Mononuclear cell collection, harvest, and transfer using a device such as the Amicus® are described in greater detail in U.S. Pat. No. 6,027,657, the contents of which are incorporated by reference herein in its entirety. Preferably, the apparatus used for the harvesting, collection and reinfusion of mononuclear cells may be a "multifunctional" automated apheresis device, as is the case with the Amicus® Separator. In other words, the separation component 10 may be a multifunctional automated apparatus that can perform various collection protocols and/or serve multiple purposes, as may be needed by a particular hospital or facility, such that it can be used not only in the systems and methods for performing photopheresis treatment of MNC as described herein, but can also be used for other purposes including the collection of blood and blood components including platelets, plasma, red blood cells, granulocytes and/or perform plasma/RBC exchange, among other functions required by the hospital or medical facility.

Figure 3:
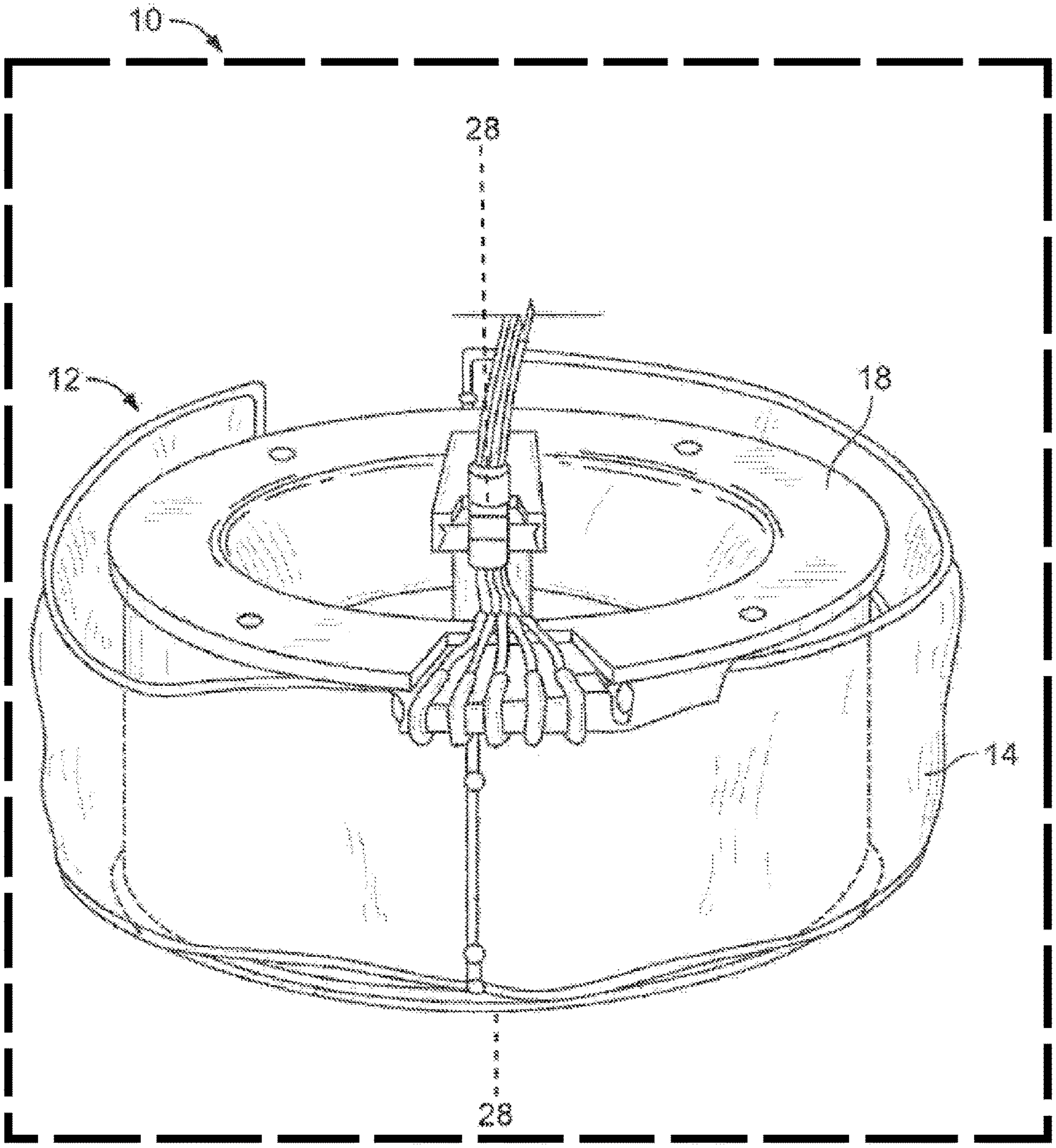
FIG. 3 is a perspective view of a separation chamber of the processing set used with the separator of FIG. 2, according to an exemplary embodiment.

FIGS. 2-4 depict a separator 10 with fluid circuit 200 mounted thereon (FIG. 2), the fluid circuit (FIG. 4) having a blood processing container 14 (FIG. 3) defining a separation chamber 12 suitable for harvesting mononuclear cells (MNC) from whole blood. As shown in FIG. 2, a disposable processing set or fluid circuit 200 (which includes container 14) may be mounted on the front panel of separator 10. The fluid circuit 200 may include a plurality of processing cassettes 23L, 23M and 23R with tubing loops for association with peristaltic pumps on separator 10. Fluid circuit 200 may also include a network of tubing and pre-connected containers for establishing flow communication with the blood source and for processing and collecting fluids and blood and blood components, as shown in FIG. 4. As seen in FIGS. 2 and 4, disposable processing set 200 may include a container 60 for supplying anticoagulant, a waste container 62 for collecting waste from one or more steps in the process for treating and washing mononuclear cells, a container 64 for holding saline or other wash or resuspension medium, a container 66 for collecting plasma, a container 68 for collecting the mononuclear cells and, optionally, container 69 for holding the photoactivation agent.

Container 68 may also serve as the illumination container, and the illumination container 68 may be pre-attached to and integral with the disposable set 200. Alternatively, container 68 may be attached to set 200 by known sterile connection techniques, such as sterile docking or the like. In FIG. 2, container 68 is shown as suspended from device 10. However, container 68 may be housed within an adjacent separately housed irradiation device 20 (as shown by broken lines in FIG. 4), thereby eliminating the step of having the operator place container 68 into irradiation device 20. The tubing leading to and/or from container 68 in fluid circuit 200 may be of a sufficient length to reach an irradiation device 20 that is adjacent to but housed separately from the separation device.

With reference to FIG. 4, fluid circuit 200 may include inlet line 72, an anticoagulant (AC) line 74 for delivering AC from container 60, an RBC line 76 for conveying red blood cells from chamber 12 of container 14 to container 67, a platelet poor plasma (PPP) line 78 for conveying PPP to container 66 and line 80 for conveying mononuclear cells to and from blood processing container 14 and collection/illumination container 68. The blood processing set may include one or more access device(s) (e.g., venipuncture needle, adapter, connector) for accessing the blood source (e.g., circulatory system of a patient, blood-filled bag). As shown in FIG. 4, fluid circuit 200 may include inlet access device 70 and return access device 82. In an alternative embodiment, a single access device may serve as both the inlet and outlet access device.

Fluid flow through fluid circuit 200 may be driven, controlled and adjusted by a microprocessor-based controller in cooperation with the valves, pumps, weight scales and sensors of device 10 and fluid circuit 200, the details of which are described in the aforementioned U.S. Pat. No. 6,027,657, although any suitable controller may be used.

In accordance with the present disclosure, the fluid circuit may be further adapted for association with the irradiation device 20. One example of a suitable irradiation device is described in U.S. Pat. No. 7,433,030, which is incorporated by reference herein in its entirety, although any suitable irradiation device may be used. The irradiation device 20 may include a tray or other holder for receiving one or more containers during treatment.

Referring to FIG. 3, separation chamber 12 is defined by the walls of a flexible processing container 14 carried within an annular gap defined by a rotating spool element 18 and an outer bowl element (not shown). The blood processing container 14 may take the form of an elongated tube which is wrapped about the spool element 18 before use. The bowl and spool element 18 may be pivoted on a yoke between an upright position and a suspended position. In operation, the separator 10 may rotate the suspended bowl and spool element 18 about an axis 28, creating a centrifugal field within the processing container 14. Details of the mechanism for causing relative movement of the spool 18 and bowl elements as described are disclosed in U.S. Pat. No. 5,360,542 entitled "Centrifuge with Separable Bowl and Spool Elements Providing Access to the Separation Chamber," which is also incorporated herein by reference in its entirety, although any suitable separation mechanism may be used.

Figure 5:
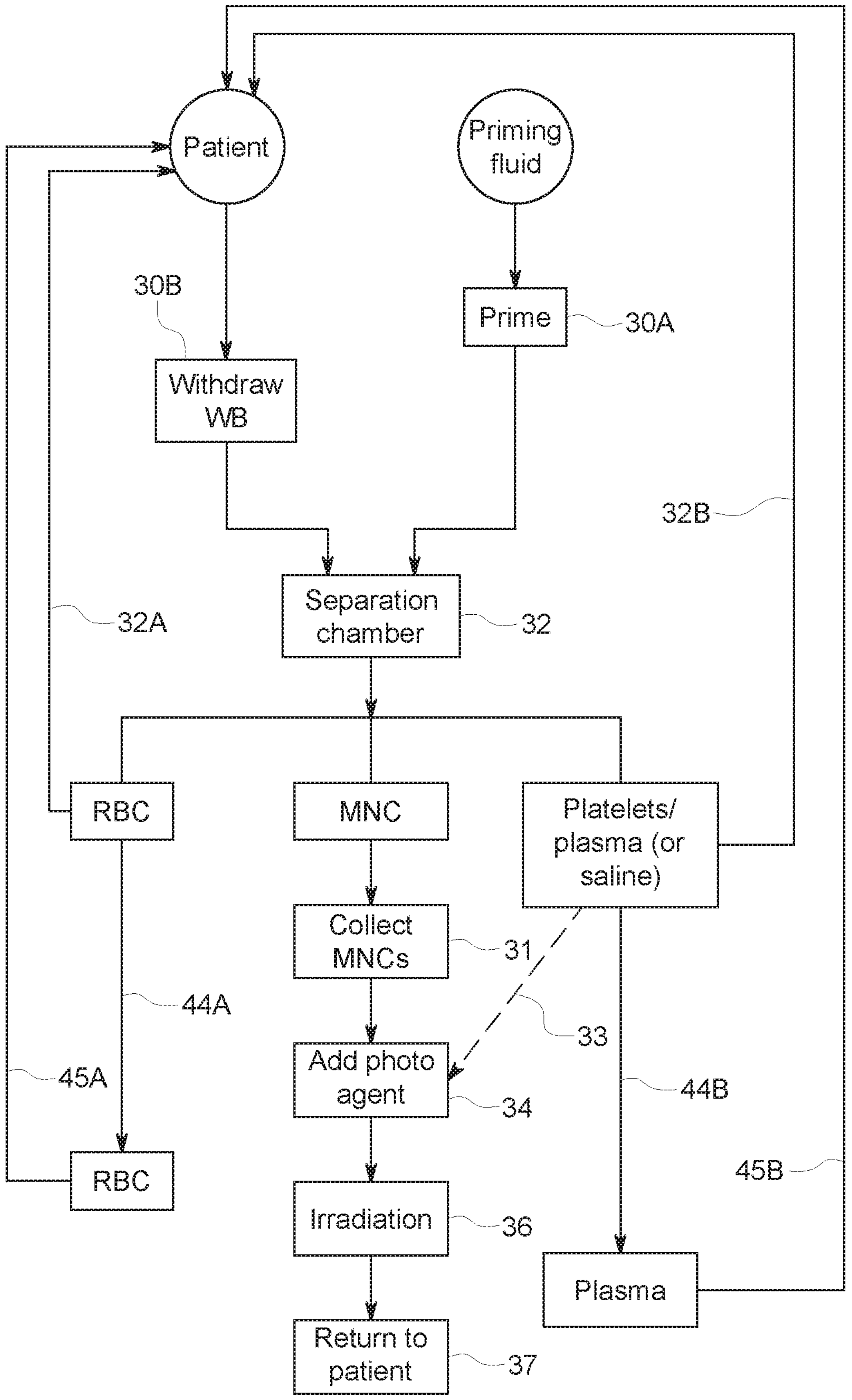
FIG. 5 is a flow chart setting forth steps of a method of an online photopheresis treatment, according to an exemplary embodiment.

FIG. 5 depicts one embodiment of an online method of treating mononuclear cells. An "online" photopheresis system includes both the blood separation device and the irradiation device in an integrated system. An online system provides for reinfusion of treated target cells back to the blood source. The fluid circuit 200 of FIG. 4 may first be primed with a priming fluid, such as saline, albumin, and/or blood components (step 30A). Whole blood may then be withdrawn from a blood source (step 30B) through inlet access device 70 (FIG. 4) and introduced into the separation chamber 12 of container 14 of processing set 200, where the whole blood is subjected to a centrifugal field. The centrifugal field may separate the target cell population, i.e., mononuclear cells, from a red blood cell constituent and a platelet/plasma constituent (step 32). A portion of the components of red blood cells and platelets/plasma may be returned to the blood source (steps 32A and 32B). Another portion of red blood cells and platelets/plasma may be diverted to other portions of the fluid circuit 200 (e.g., container 67 for RBCs, container 66 for plasma/platelets) for further utilization and/or processing (steps 44A and 44B). Collection of the mononuclear cells may proceed in one or more cycles comprising steps 30B, 32, 32A, 32B, 44A, and 44B, with the number of processing cycles conducted in a given therapeutic procedure depending upon the total yield of MNCs to be collected and/or the desired volume of whole blood to be processed. Once the desired number of cycles has taken place, the MNCs accumulated in the separation chamber 12 may be collected (step 31). A photoactivation agent may be added to the collected MNCs (step 34), and the MNCs may be irradiated (step 36). The portion of red blood cells and platelets/plasma that were diverted to other portions of the fluid circuit 200 in steps 44A and 44B may be reinfused into the blood source (steps 45A and 45B) while the MNCs are being irradiated in step 36, or they may be reinfused during reinfusion of the irradiated MNCs into the blood source (step 37).

Although FIG. 5 depicts an online method of treating MNCs, offline methods are available as well. In offline methods, an apheresis device may be used to collect target cells. The collected target cells, typically contained in one or more collection containers, are severed or otherwise separated from the tubing set used during collection, where they are later treated in a separate irradiation or UVA light device followed by subsequent reinfusion of the treated cells to a blood source. During such offline methods, when the cells are transferred from the apheresis device to the irradiation device (which device may be located in another room or laboratory), communication with the blood source is severed and the cells detached from the blood source.

Effective treatment of the MNCs with light may be facilitated by collecting mononuclear cells in a suspension having a suitable hematocrit, volume, and/or thickness. The hematocrit, volume, and/or thickness of the MNC suspension to be treated may affect the amount of UV light absorbed by the MNCs, given that the red blood cells in the MNC suspension block at least a portion the UV light from reaching the targeted MNCs. Control of hematocrit may be desirable in cases in which the light source of the irradiation device is configured to irradiate a set intensity of light, limited settings of light intensity values, and/or a set dose of irradiation, although hematocrit/thickness control may be desirable also in cases in which intensity, dose, and/or exposure settings may readily be adjusted according to hematocrit. It is common for a transmitter (e.g., bank of light bulbs) of an irradiation device to not be adjustable in terms of intensity of emission and therefore may emit a near-constant intensity of light. If the hematocrit of the suspended MNCs is too high (such that the red blood cells prevent the absorption of light by the MNCs), it may be desired to dilute the mononuclear cells with a diluting solution, such as plasma or saline, as shown in step 33 (FIG. 5), to control the hematocrit, volume, and/or thickness so that a desired amount of UV light will reach the targeted MNC. The diluted mononuclear cells (in container 68) may then be combined with the suitable photoactivation agent in step 34.

A procedure may often involve introducing fluids into the fluid circuit in excess of the optimal fluid volume to be reinfused into the blood source. For example, saline may be introduced into the fluid circuit 200 (FIG. 4) at the initial priming stage (e.g., step 30A of FIG. 5). Saline may also be added to the MNC suspension (e.g., step 33). Anticoagulant may be added to whole blood during the draw process (e.g., step 30B of FIG. 5). Reinfusing treated cells and fluid remaining in the fluid circuit may result in a blood source's fluid balance at the end of the procedure being positive, e.g., approximately 600 to 800 mL more than initial blood volume prior to the procedure. For certain blood sources for which even small positive changes in total fluid volume are undesirable, e.g., lung transplant patients, products intended for lunch transplant patients, it may be desirable to maintain a close to constant total blood volume before and after the procedure. In one embodiment, in order to minimize changes in total fluid volume, treated cells may be reinfused, and only a portion of the blood components and other fluids remaining in the fluid circuit may be reinfused (steps 45A, 45B). In another embodiment, treated cells may be reinfused without reinfusing any of the blood components and other fluids remaining in the fluid circuit.

Figure 6:
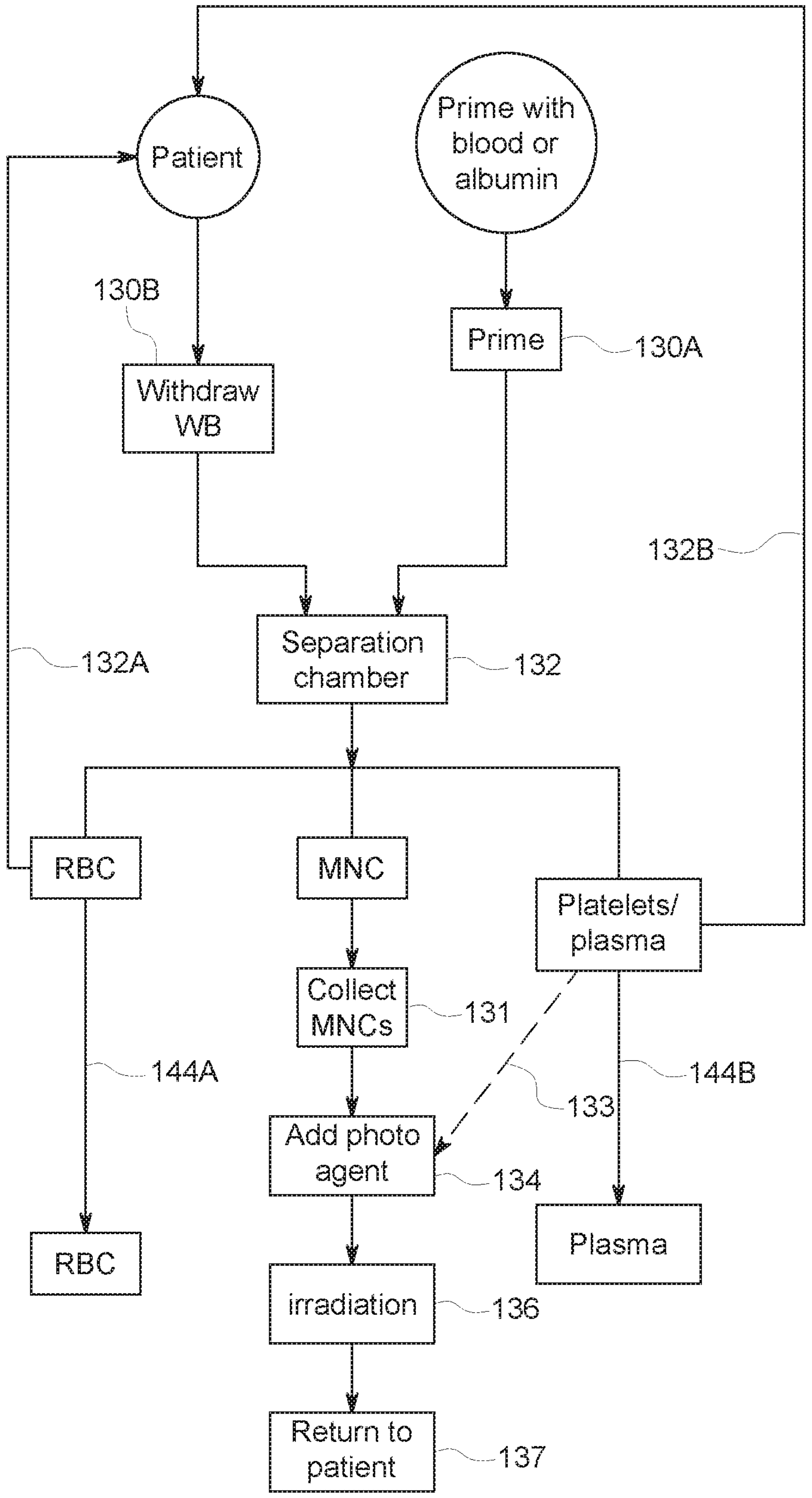
FIG. 6 is a flow chart setting forth steps of a method of an online photopheresis treatment without reinfusion of blood components and other fluids remaining in the fluid circuit, according to an exemplary embodiment.

FIG. 6 depicts one embodiment of a method of treating mononuclear cells without reinfusing any of the blood components and other fluids remaining in the fluid circuit. Reinfusion of blood components and other fluids remaining in the fluid circuit may not be desirable, e.g., when blood components and/or albumin is used as a priming fluid. Priming with blood components and/or albumin may be desirable for a blood source associated with patients with low total blood volumes so that blood is returned to the blood source as blood is being drawn out from the blood source. An undesirable drop in total blood volume may thereby be prevented at the beginning of the procedure. The fluid circuit 200 of FIG. 4 may first be primed with albumin and/or blood components (step 130A). Whole blood may then be withdrawn from a blood source (step 130B) through inlet access device 70 (FIG. 4) and introduced into the separation chamber 12 of container 14 of processing set 200, where the whole blood is subjected to a centrifugal field. The centrifugal field may separate the target cell population, i.e., mononuclear cells, from a red blood cell constituent and a platelet/plasma constituent (step 132). A portion of the components of red blood cells and platelets/plasma may be returned to the blood source (steps 132A and 132B) into whole blood. Another portion of red blood cells and platelets/plasma may be diverted to other portions of the fluid circuit 200 (e.g., container 67 for RBCs, container 66 for plasma/platelets) for further utilization and/or processing (steps 144A and 144B). A portion of plasma and/or saline may be added to the collected MNCs (step 133) to achieve a desired hematocrit, volume, and/or thickness. Collection of the mononuclear cells may proceed in one or more cycles comprising the steps 130B, 132, 132A, 132B, 144A, and 144B, with the number of processing cycles conducted in a given therapeutic procedure depending upon the total yield of MNCs to be collected and/or the desired volume of whole blood to be processed. Once the desired number of cycles has taken place, the MNCs accumulated in the separation chamber 12 may be collected (step 131). A photoactivation agent may be added to the collected MNCs (step 134), and the MNCs may be irradiated (step 136) and then returned to the patient (step 137). The portion of red blood cells and platelets/plasma that were diverted to other portions of the fluid circuit 200 in steps 144A and 144B may be discarded or retained for further use without returning to the blood source. In the event it is desired for access to the blood source (e.g., vein access to a patient) to remain open during the irradiation step 136, a slowly-pumped saline drip (or other suitable fluid) may be maintained at the return line 82 of FIG. 4.

Figure 7:
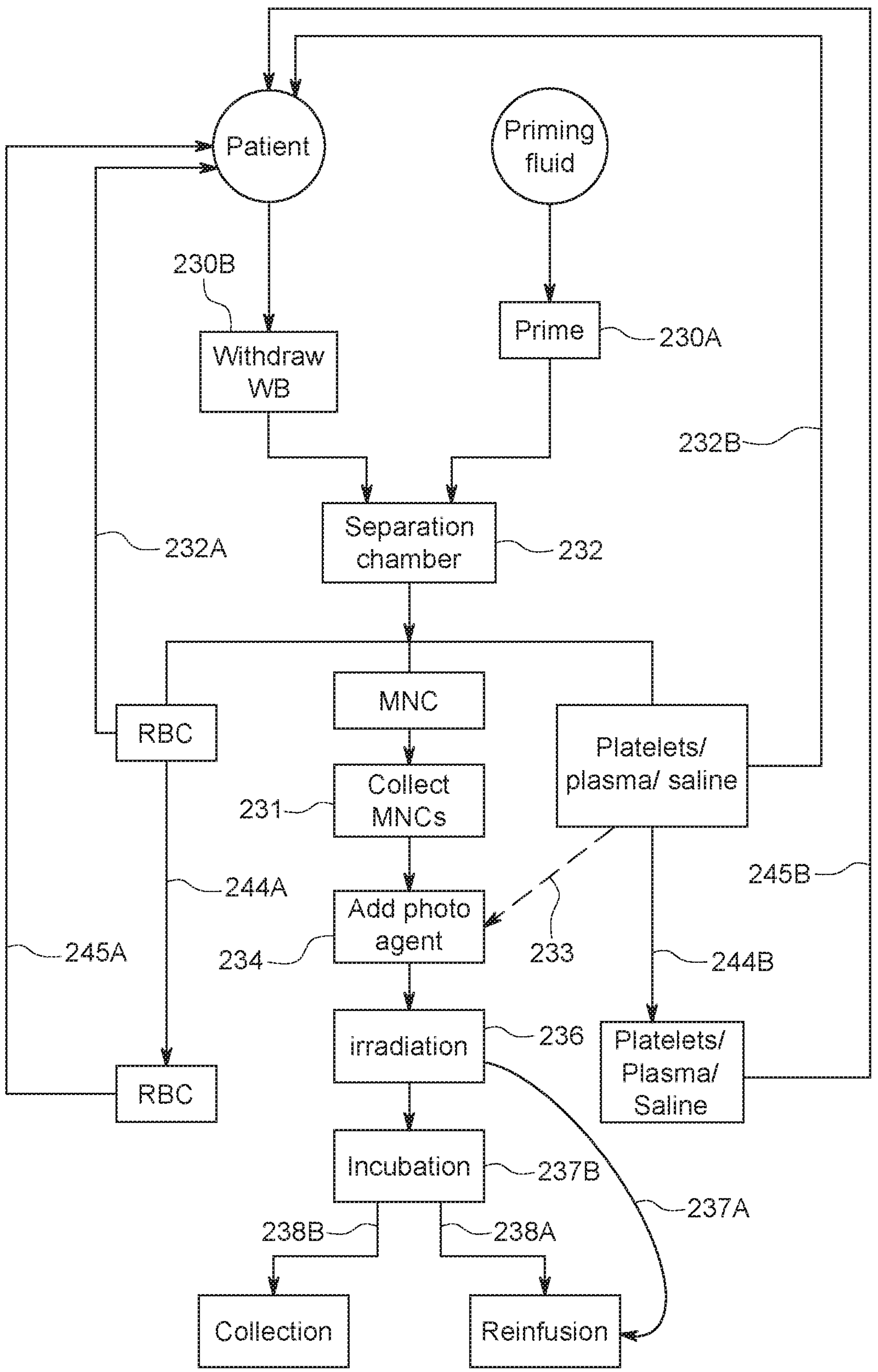
FIG. 7 a flow chart setting forth steps of a method of an online photopheresis treatment with incubation of irradiated mononuclear cells, according to an exemplary embodiment.

FIG. 7 depicts one embodiment of a method of treating mononuclear cells, incubating apoptotic T-cells with monocytes to optimize differentiation into dendritic cells, and reinfusing all, part, or none of the apoptotic T-cells and dendritic cells into a blood source after the incubation period. The fluid circuit 200 of FIG. 4 may be primed with a priming fluid, such as saline, albumin, and/or blood components (step 230A). Whole blood may then be withdrawn from a blood source (step 230B) through inlet access device 70 (FIG. 4) and introduced into the separation chamber 12 of container 14 of processing set 200, where the whole blood is subjected to a centrifugal field. The centrifugal field may separate the target cell population, i.e., mononuclear cells, from a red blood cell constituent and a platelet/plasma constituent (step 232). A portion of the components of red blood cells and platelets/plasma may be returned to the blood source (steps 232A and 232B) for recirculation into whole blood. Another portion of red blood cells and platelets/plasma may be diverted to other portions of the fluid circuit 200 (e.g., container 67 for RBCs, container 66 for plasma/platelets) for further utilization and/or processing (steps 244A and 244B). A portion of platelets/plasma/saline may be added to the collected MNCs (step 233) to achieve a desired hematocrit, volume, and/or thickness. Collection of the mononuclear cells may proceed in one or more cycles comprising steps 230B, 232, 232A, 232B, 244A, and 244B, with the number of processing cycles conducted in a given therapeutic procedure depending upon the total yield of MNCs to be collected and/or the desired volume of whole blood to be processed. Once the desired number of cycles has taken place, the MNCs accumulated in the separation chamber 12 may be collected (step 231). A photoactivation agent may be added to the collected MNCs (step 234), and the MNCs may be irradiated (step 236). The portion of red blood cells and platelets/plasma that were diverted to other portions of the fluid circuit 200 in steps 244A and 244B may be reinfused into the blood source (steps 245A and 245B) while the MNCs are being irradiated in step 236. After irradiation, all or some of the MNCs may be incubated (step 237B) for a period of time to allow for apoptotic T-cells generated by irradiation to induce monocytes to differentiate into dendritic cells. In an embodiment in which only some of the MNCs are incubated, the remaining irradiated MNCs may be reinfused into the blood source (step 237A). The incubation period and/or cell volume may be dependent on the apoptosis profile desired and/or the disease state sought to be treated. In one embodiment, the incubation period may be overnight (e.g., at least 12 hours) or multiple days. In an embodiment in which all of the MNCs are incubated, the blood source may be disconnected from the system 5 (FIG. 1) during the incubation period. In an embodiment in which some of the MNCs are reinfused without incubation, the blood source may be disconnected from the system after reinfusion (step 237A).

In one embodiment, all of the incubated MNCs may be collected (step 238B of FIG. 7), in which case a blood source may not receive any reinfusion of treated cells. In another embodiment, after the incubation period, the blood source may be reconnected to the system and be reinfused with all of the incubated MNCs (step 238A) containing apoptotic T-cells and recently-differentiated dendritic cells. In another embodiment, after the incubation period, the blood source may be reconnected to the system and be reinfused with a portion of the incubated MNCs (step 238A), while the other portion is collected (step 238B). Partial reinfusion of the treated cells may be performed if, e.g., a portion is desired for research purposes, a disease state calls for an optimum dosage of treated cells for reinfusion less than the total amount of treated cells available, etc.

Without limiting the foregoing description, in accordance with one aspect of the subject matter herein, there is provided method for treating mononuclear cells for an extracorporeal photopheresis procedure, driven and adjusted by a microprocessor-based controller. A fluid circuit is primed with priming fluid. Whole blood derived from a blood source is directed into the fluid circuit. The whole blood is separated into a red blood cell component, a mononuclear cell component, and a plasma component. A first portion of the red blood cell component and a first portion of the plasma component are returned to the whole blood. A photoactivation agent is added to the mononuclear cell component to create an agent-added mononuclear cell component. The agent-added mononuclear cell component is irradiated to create a photoactivated mononuclear cell component. A first portion of the photoactivated mononuclear cell component is incubated for a period of time to create an incubated photoactivated mononuclear cell component.

In accordance with a second aspect which may be used or combined with the immediately preceding aspect, a second portion of the red blood cell component and a second portion of the plasma component are retained within the fluid circuit prior to adding the photoactivation agent. The second portion of the red blood cell component and the second portion of the plasma component are reinfused into the blood source.

In accordance with a third aspect which may be used or combined with any of the preceding aspects, the priming fluid comprises at least one of albumin and a blood component.

In accordance with a fourth aspect which may be used or combined with the second aspect, the priming fluid comprises saline.

In accordance with a fifth aspect which may be used or combined with any of the second and fourth aspects, the second portion of the red blood cell component and the second portion of the plasma component are reinfused into the blood source at the same time as irradiating the agent-added mononuclear cell component.

In accordance with a sixth aspect which may be used or combined with any of the preceding aspects, the blood source is disconnected from the fluid circuit for at least a portion of the period of time.

In accordance with a seventh aspect which may be used or combined with any of the preceding aspects, a second portion of the photoactivated mononuclear cell component is reinfused without incubating the second portion.

In accordance with an eighth aspect which may be used or combined with any of the preceding aspects, a first portion of the incubated photoactivated mononuclear cell component is reinfused to the blood source.

In accordance with a ninth aspect which may be used or combined with the eighth aspect, a second portion of the incubated photoactivated mononuclear cell component is collected without reinfusion to the blood source.

In accordance with a tenth aspect which may be used or combined with any of the preceding aspects, none of the incubated photoactivated mononuclear cell component is reinfused to the blood source.

In accordance with an eleventh aspect, there is provided a system for treating mononuclear cells for an extracorporeal photopheresis procedure. A disposable fluid circuit comprises a product container configured to receive a mononuclear cell component and a priming fluid container configured to receive albumin and/or a blood component for priming the disposable fluid circuit. A separator is configured to work in association with the disposable fluid circuit. The separator comprises a chamber configured to rotate about a rotational axis and convey whole blood into an inlet region of the chamber for separation into a red blood cell component, a plasma component, and the mononuclear cell component. A microprocessor-based controller is in communication with the separator. The controller is configured to direct the priming fluid from the priming fluid container through the disposable fluid circuit. Whole blood derived from a blood source is directed into the disposable fluid circuit while a portion of the priming fluid is returned to the blood source. The whole blood is separated into the red blood cell component, the mononuclear cell component, and the plasma component. A first portion of the red blood cell component and a first portion of the plasma component are returned to the blood source to the whole blood. A second portion of the red blood cell component and a second portion of the plasma component are retained within the fluid circuit without returning to the blood source. The mononuclear cell component is directed to the product container. The product container comprising the mononuclear cell component and a photoactivation agent is irradiated to create a photoactivated mononuclear cell component. The photoactivated mononuclear cell component is reinfused to the blood source.

In accordance with a twelfth aspect which may be used or combined with the eleventh aspect, the controller is further configured to add a part of the second portion of the plasma component to mononuclear cell component to achieve a desired hematocrit, volume, and/or thickness.

In accordance with a thirteenth aspect which may be used or combined with any of the eleventh and twelfth aspects, the disposable fluid circuit further comprises a saline container in communication with the blood source, wherein the controller is further configured to maintain a saline drip from the saline container to the blood source during irradiation of the product container.

In accordance with a fourteenth aspect which may be used or combined with any of the eleventh through thirteenth aspects, the controller is further configured to incubate for a period of time the photoactivated mononuclear cell component prior to reinfusing the photoactivated mononuclear cell component to the blood source.

In accordance with a fifteenth aspect which may be used or combined with any of the eleventh through fourteenth aspects, the period of time comprises at least twelve hours.

In accordance with a sixteenth aspect, there is provided a method for treating mononuclear cells for an extracorporeal photopheresis procedure, driven and adjusted by a microprocessor-based controller. Whole blood derived from a blood source is directed into a fluid circuit. The whole blood is separated into a red blood cell component, a mononuclear cell component, and a plasma component. A first portion of the red blood cell component and a first portion of the plasma component are returned to the whole blood. A second portion of the red blood cell component and a second portion of the plasma component are retained within the fluid circuit. A photoactivation agent is added to the mononuclear cell component to create an agent-added mononuclear cell component. The agent-added mononuclear cell component is irradiated to create a photoactivated mononuclear cell component comprising apoptotic T-cells and monocytes. The second portion of the red blood cell component and the second portion of the plasma component are reinfused into the blood source. A portion of the photoactivated mononuclear cell component is incubated for a period of time to induce differentiation of the monocytes into dendritic cells. The blood source is disconnected from the fluid circuit while the portion of the photoactivated mononuclear cell component is incubating. A portion of the incubated photoactivated mononuclear cell component is reinfused to the blood source.

In accordance with a seventeenth aspect which may be used or combined with the sixteenth aspect, a saline drip to the blood source is maintained while irradiating the agent-added mononuclear cell component.

In accordance with an eighteenth aspect which may be used or combined with any of the sixteenth or seventeenth aspects, the incubated photoactivated mononuclear cell component comprises apoptotic T-cells and dendritic cells.

In accordance with a nineteenth aspect which may be used or combined with any of the sixteenth through eighteenth aspects, reinfusing into the blood source the second portion of the red blood cell component and the second portion of the plasma component takes place at the same time as irradiating the agent-added mononuclear cell component.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A method for treating mononuclear cells for an extracorporeal photopheresis procedure, driven and adjusted by a microprocessor-based controller, comprising the steps of:

priming a fluid circuit with priming fluid;

directing whole blood derived from a blood source into the fluid circuit;

separating the whole blood in a separation chamber of the fluid circuit into a red blood cell component, a mononuclear cell component, and a platelet/plasma component;

returning a first portion of the red blood cell component and a first portion of the platelet/plasma component to the whole blood at the same time as the mononuclear cell component is accumulating in the separation chamber;

adding a biological agent to the mononuclear cell component in an illumination container fluidically connected to the separation chamber to create an agent-added mononuclear cell component;

irradiating the agent-added mononuclear cell component in an illumination container of the fluid circuit; and after irradiation of the agent-added mononuclear cell component has ended, incubating for a period of time a first portion of the agent-added mononuclear cell component in the illumination container to create an incubated agent-added mononuclear cell component, with the blood source being disconnected from the fluid circuit for at least a portion of the period of time, wherein the period of time is sufficiently long to allow for apoptotic T-cells generated in the agent-added mononuclear cell component by irradiation to induce differentiation of monocytes in the first portion of the agent-added mononuclear cell component into dendritic cells, and a single fluid circuit is used for both separating the whole blood and incubating the first portion of the agent-added mononuclear cell component.

2. The method of claim 1, further comprising:

retaining a second portion of the red blood cell component and a second portion of the platelet/plasma component within the fluid circuit prior to adding the biological agent; and reinfusing into the blood source the second portion of the red blood cell component and the second portion of the platelet/plasma component.

3. The method of claim 1, wherein the priming fluid comprises at least one of albumin and a blood component.

4. The method of claim 1, wherein the priming fluid comprises saline.

5. The method of claim 1, wherein the biological agent comprises a photoactivation agent, the agent-added mononuclear cell component is irradiated to create a photoactivated mononuclear cell component prior to incubation, and said incubating for a period of time a first portion of the agent-added mononuclear cell component in the illumination container to create an incubated agent-added mononuclear cell component comprises incubating for said period of time a first portion of the photoactivated mononuclear cell component in the illumination container to create an incubated photoactivated mononuclear cell component.

6. The method of claim 1, further comprising retaining a second portion of the red blood cell component and a second portion of the platelet/plasma component within the fluid circuit without returning to the blood source.

7. The method of claim 5, further comprising disconnecting the blood source from the fluid circuit while incubating said first portion of the photoactivated mononuclear cell component.

8. The method of claim 7, further comprising reinfusing a portion of the incubated photoactivated mononuclear cell component into the blood source.

9. The method of claim 1, further comprising washing at least a portion of the incubated agent-added mononuclear cell component.

10. The method of claim 1, further comprising returning a portion of the priming fluid to the blood source.

11. The method of claim 1, further comprising reinfusing a second portion of the agent-added mononuclear cell component.

12. The method of claim 1, further comprising reinfusing a first portion of the incubated agent-added mononuclear cell component to the blood source.

13. The method of claim 12, further comprising collecting a second portion of the incubated agent-added mononuclear cell component without reinfusion to the blood source.

14. The method of claim 1, further comprising reinfusing none of the incubated agent-added mononuclear cell component to the blood source.

15. The method of claim 5, further comprising retaining a second portion of the red blood cell component and a second portion of the platelet/plasma component within the fluid circuit prior to adding the photoactivation agent, and reinfusing into the blood source the second portion of the red blood cell component and the second portion of the platelet/plasma component at the same time as irradiating the agent-added mononuclear cell component.

16. The method of claim 5, further comprising reinfusing a second portion of the photoactivated mononuclear cell component.

17. The method of claim 5, further comprising reinfusing a first portion of the incubated photoactivated mononuclear cell component to the blood source.

18. The method of claim 17, further comprising collecting a second portion of the incubated photoactivated mononuclear cell component without reinfusion to the blood source.

19. The method of claim 5, further comprising reinfusing none of the incubated photoactivated mononuclear cell component to the blood source.

20. The method of claim 1, wherein the whole blood is directed into the fluid circuit via an access device of the fluid circuit connected to the blood source, and the blood source is disconnected from the access device of the fluid circuit for said at least a portion of the period of time.

* * * * *